United States Patent

Kihara et al.

[11] Patent Number: 4,766,304
[45] Date of Patent: Aug. 23, 1988

[54] SENSITIVITY-CALIBRATION CIRCUIT FOR USE IN AN ABSORPTION ANALYZER

[75] Inventors: Nobutaka Kihara; Ichiro Asano; Kennosuke Kojima, all of Kyoto, Japan

[73] Assignee: Horiba, Ltd., Kyoto, Japan

[21] Appl. No.: 906,016

[22] Filed: Sep. 11, 1986

[30] Foreign Application Priority Data

Nov. 9, 1985 [JP] Japan ................. 60-251524

[51] Int. Cl.$^4$ .......................... H01J 40/14
[52] U.S. Cl. ...................... 250/214 C; 307/310
[58] Field of Search .......... 250/214 R, 214 A, 214 C, 250/208, 209, 206, 573; 356/218, 223, 226; 307/310; 323/906, 907

[56] References Cited

U.S. PATENT DOCUMENTS 3,783,300  1/1974  Johnson ................. 250/214 C
3,988,682  10/1976  Mikonis ..................... 307/310

*Primary Examiner*—David C. Nelms
*Attorney, Agent, or Firm*—Wenderoth, Lind & Ponack

[57] ABSTRACT

A sensitivity calibration circuit for use in an absorption analyzer provided with a check-signal generator for easily checking the sensitivity, includes a temperature compensating circuit for use in an optical system for compensating for a temperature draft due to said optical system and a temperature compensation circuit for use in a sample system for compensating for a temperature draft due to the sample system. The temperature compensation circuit for use in an optical system and the temperature compensation circuit for use in a sample system are separately provided and a switch is provided which is switchable to a measuring state in which both the temperature compensation circuit for use in an optical system and the temperature compensation circuit for use in a sample system are used and is switchable to a checking state in which the temperature compensation circuit for use in a sample system is disconnected so as not to be used but the temperature compensation circuit for use in an optical system is used.

2 Claims, 3 Drawing Sheets

SENSITIVITY-CALIBRATION CIRCUIT FOR USE IN AN ABSORPTION ANALYZER

BACKGROUND OF THE INVENTION

1. Field of the Invention

The present invention relates to a sensitivity-calibration circuit for use in an absorption analyzer, such as non-dispersion type infrared analyzer, colorimetric analyzer and spectrophotometric analyzer; more particularly, for use in an absorption analyzer provided with a check-signal generating mechanism arranged so that the sensitivity can be easily checked without requiring the continuous use of a span-calibration sample.

2. Description of the Prior Art

FIG. 3(A) shows one example of a fundamental non-dispersion type absorption analyzer for use in gas analysis. A cell b, into which a sample gas and a zero gas are alternately introduced by a three-way valve d, and a sample-concentration detector c are arranged in an optically linear relationship relative to a light source a capable of irradiating infrared beams and a check-signal generating mechanism f comprising a potentiometric circuit called an "elechecker" is provided between a preamplifier e of said sample-concentration detector c and a sensitivity-calibration circuit g so that the sensitivity can be easily checked without requiring the continuous use of a span-calibration sample (span gas). That is to say, this elechecker type check-signal generating mechanism f is adapted so as to be switched over to one state, in which an output signal (sample-concentration signal $V_G$) from the preamplifier e of said sample-concentration detector c is fed to the sensitivity-calibration circuit g as is, during the time that a measurement is carried out by introducing a sample into said cell b, and another state in which a check signal $V_c$ obtained by dividing the output signal from said preamplifier e by an appointed ratio is fed to said sensitivity-calibration circuit g during the time that an easy check is carried out by introducing only a zero gas into said cell b.

In addition, a "mechachecker" comprising a light-reducing filter and a screen plate, which can be inserted between the light source a and the cell b (or between the cell b and the sample-concentration detector c), as shown FIG. 3(B), can be used as the check-signal generating mechanism f in addition to said elechecker comprising a potentiometric circuit. In the case of an absorption analyzer provided with this mechachecker type check-signal generating mechanism f, the sample-concentration signal $V_G$ is obtained from the preamplifier of said sample-concentration detector c to be fed to said sensitivity-calibration circuit g by pulling said light-reducing filter of the mechachecker out of the optical path, as shown by a dotted line in FIG. 3(B), and during the time that the measurement is carried out by introducing the sample into said cell b while the check signal $V_c$ obtained from the preamplifier e of said sample-concentration detector c is fed to the sensitivity-calibration circuit g by inserting said light-reducing filter into an optical path, as shown by a solid line in FIG. 3(B), inserting the screen plate into the optical path to an appointed extent in the easy check carried out by introducing only the zero gas into said cell b.

The sensitivity-calibration circuit g, to which said sample-concentration signal $V_G$ or said check signal $V_c$ is supplied as an input signal $V_{IN}$, comprises an operational amplifier $O_o$ and a thermosensor Th and been provided with a temperature-compensation circuit $A_o$ for compensating for a temperature-drift of the input signal $V_{IN}$ on the basis of a detected result by the thermosensor Th and a sensitivity-adjustment circuit C comprising an operational amplifier $O_3$ and a sensitivity-adjustment potentiometer VR, as shown in FIG. 4.

However, with the sensitivity-calibration circuit in the absorption analyzer having a conventional construction as shown in FIG. 4, the following disadvantages have occurred.

Since the temperature-drift of the output signal from an analytical portion (the input signal $V_{IN}$ to the sensitivity-calibration circuit g) is roughly classified into one drift due to the sample system such as a change in density of the sample itself and one drift due to the optical system such as a change in the output of the light source a and a change in sensitivity of the sample-concentration detector c due to temperature-changes, and the sensitivity-calibration circuit having the conventional construction is provided with only one temperature-compensation circuit $A_o$ in spite of a difference in temperature-change rate between the temperature-drift due to the sample system and the temperature-drift due to the optical system. In other words, the temperature-drift due to the sample system and the temperature-drift due to the optical system are intended to be collectively compensated. The temperature-compensation circuit $A_o$ normally operates in a regular sensitivity-calibration and a usual measurement using a span-calibration sample but the temperature-compensation circuit $A_o$ does not normally operate, whereby the system is incapable of achieving an accurate sensitivity-check or sensitivity-calibration in the easy check without using the span-calibration sample. In short, only the zero gas is sent to said cell b in said easy check, so that in fact the temperature-drift due to said sample system is not produced. Nevertheless, a so called excessive temperature-compensation is carried out as if the temperature-drift due to the sample system existed.

This will be better understood from the description using the following equations:

Provided that a temperature-drift function of the optical system is f(t) and a temperature-drift of the sample system is g(t), the sample-concentration signal $V_G$ and the check signal $V_c$ is expressed by the following equations, respectively.

$$V_G = c_1 \cdot f(t) \cdot g(t)$$

$$V_c = c_2 \cdot f(t)$$

wherein $c_1$ and $c_2$ constants.

The gain of the temperature-compensation circuit $A_o$ is adjusted to $K/ f(t) \cdot g(t)$ in this case. Accordingly, provided that a gain of said sensitivity-adjustment circuit C is expressed by G(VR), a total gain $G_T$ of the sensitivity-calibration circuit g is expressed by the following equation:

$$G_T = G(VR) \cdot K/ f(t) \cdot g(t)$$

Consequently, the output signal $V_{OUT}$ from the sensitivity-calibration circuit g in the regular sensitivity-calibration and the usual measurement using the span-calibration sample is expressed by the following equation:

$$V_{OUT} = V_G \cdot G_T$$
$$= c_1 \cdot f(t) \cdot g(t) \times G(VR) \cdot K/f(t) \cdot g(t)$$
$$= c_1 \cdot G(VR) \cdot K$$

whereby an influence by temperature is eliminated but an output signal $V_{OUT}$ from the sensitivity-calibration circuit g in said easy check without using the span-calibration sample is expressed by the following equation:

$$V_{OUT} = V_c \cdot G_T$$
$$= c_2 \cdot f(t) \times G(VR) \cdot K/f(t) \cdot g(t)$$
$$= c_2 \cdot G(VR) \cdot K/g(t)$$

Accordingly, temperature influences due to g(t) appear.

SUMMARY OF THE INVENTION

It is an object of the present invention to provide a sensitivity-calibration circuit for use in an absorption analyzer capable of always carrying out a normal temperature-compensation in not only a regular sensitivity-calibration and a usual measurement using a span-calibration sample but also in an easy check without using the span-calibration sample.

In order to achieve the above described object, a sensitivity-calibration circuit for use in an absorption analyzer according to the present invention comprises a temperature-compensation circuit A for use in an optical system for compensating for a temperature-drift due to the optical system, and a temperature-compensation circuit B for use in a sample system for compensating for a temperature-drift due to the sample system; the temperature-compensation circuit for use in an optical system and the temperature-compensation circuit for use in a sample system are separately provided, and a switch SW capable of being switched to a measuring state, in which both the temperature-compensation circuit A for use in an optical system and the temperature-compensation circuit B for use in a sample system are used, and switched to a checking state in which the temperature-compensation circuit A for use in an optical system is used without using the temperature-compensation circuit B for use in a sample system.

Referring now to FIGS. 1(A) and 1(B), C designates a sensitivity-adjustment circuit; $O_1$, $O_2$, and $O_3$ respectively designate operational amplifiers; $Th_o$ and $Th_G$ respectively designate thermosensors, and VR designates a sensitivity-adjustment potentiometer.

The effects exhibited by the above described circuits are as follows:

With a sensitivity-calibration circuit for use in an absorption analyzer according to the present invention, a temperature-drift due to a sample system and a temperature-drift due to an optical system are not intended to be collectively compensated as in a sensitivity-calibration circuit having the conventional construction but a temperature-compensation circuit A for use in an optical system and a temperature-compensation circuit B for use in a sample system are separately provided and a sample-concentration signal $V_G$ used as an input signal $V_{IN}$ can be passed through both the temperature-compensation circuit A for use in an optical system and the temperature-compensation circuit B for use in a sample system by arranging the switch SW so as to be at a concentration-measuring side during a regular sensitivity-calibration and during a usual measurement which the check signal $V_c$ used as the input signal $V_{IN}$ can be passed through only the temperature-compensation circuit B for use in a sample system without passing through the temperature-compensation circuit A for use in an optical system by arranging said switch SW so as to be at a check side during an easy check without using the span-calibration sample, as shown in FIGS. 1(A) and 1(B). Thus, each temperature-drift may be separately treated and a normal temperature-compensation can be achieved only not during a regular sensitivity-calibration and during a usual measurement using a span-calibration sample but also during an easy check without using the span-calibration sample, whereby an accurate sensitivity-check or sensitivity-calibration can always be achieved.

In addition, describing this in accordance with equations, in a fashion similar to the description noted above, provided that a temperature-drift function of the optical system is f(t) and a temperature-drift function of the sample system is g(t), the sample-concentration signal $V_G$ and the check signal $V_c$ are expressed by the following equations:

$$V_G = c_1 \cdot f(t) \cdot g(t)$$

$$V_c = c_2 \cdot f(t)$$

wherein $c_1$ and $c_2$ are constant.

Since a gain of said temperature-compensation circuit A for use in an optical system is adjusted to $K_1/f(t)$ and a gain of said temperature-compensation circuit B for use in a sample system is adjusted to $K_2/g(t)$ in this case, provided that a gain of a sensitivity-adjustment circuit C is expressed by G(VR), a total gain $G_{TS}$ of the sensitivity-calibration circuit is expressed by the following equation in the case where the switch SW is arranged so as to be at a concentration-measuring side:

$$G_{TS} = G(VR) \cdot K_1 \cdot K_2/f(t) \cdot g(t)$$

Consequently, an output signal $V_{OUT}$ from the sensitivity-calibration circuit during a regular sensitivity-calibration and during a usual measurement using a span-calibration sample is expressed by the following equation:

$$V_{OUT} = V_G \cdot G_{TS}$$
$$= c_1 \cdot f(t) \cdot g(t) \times G(VR) K_1 K_2/f(t) \cdot g(t)$$
$$= c_1 \cdot G(VR) \cdot K_1 \cdot K_2$$

whereby an influence by temperature is eliminated while a total gain $G_{TC}$ of the sensitivity-calibration circuit in the case where the switch SW is arranged so as to be at a check side and the temperature-compensation circuit B is not used, is expressed by the following equation:

$$G_{TC} = G(VR) \cdot K_1/f(t)$$

Accordingly, an output signal $V_{OUT}$ from the sensitivity-calibration circuit during the easy check without using the span-calibration sample is expressed by the following equation:

$$V_{OUT} = V_c \cdot G_{TC}$$
$$= V_c \cdot G(VR) \cdot K_1/f(t)$$
$$= c_2 \cdot G(VR) \cdot K_1$$

whereby temperature influence can also be eliminated in this case.

Since a sensitivity-calibration circuit in an absorption analyzer according to the present invention comprises a temperature-compensation circuit for use in an optical system for compensating for a temperature-drift due to an optical system, a temperature-compensating circuit for use in a sample system for compensating for a temperature-drift due to a sample system and a switch capable of being switched over to a measuring state, in which both the temperature-compensating circuit for use in an optical system and the temperature-compensating circuit for use in a sample system are used, and a checking state in which the temperature-compensating circuit for use in a sample system is not used but the temperature-compensating circuit for use in an optical system is used, a normal temperature-compensation can be achieved not only during a regular sensitivity-calibration and a usual measurement using the span-calibration sample but also during an easy check without using the span-calibration sample, whereby an accurate sensitivity-check or sensitivity-calibration is always achieved.

DESCRIPTION OF THE PREFERRED EMBODIMENT

Figure 2:
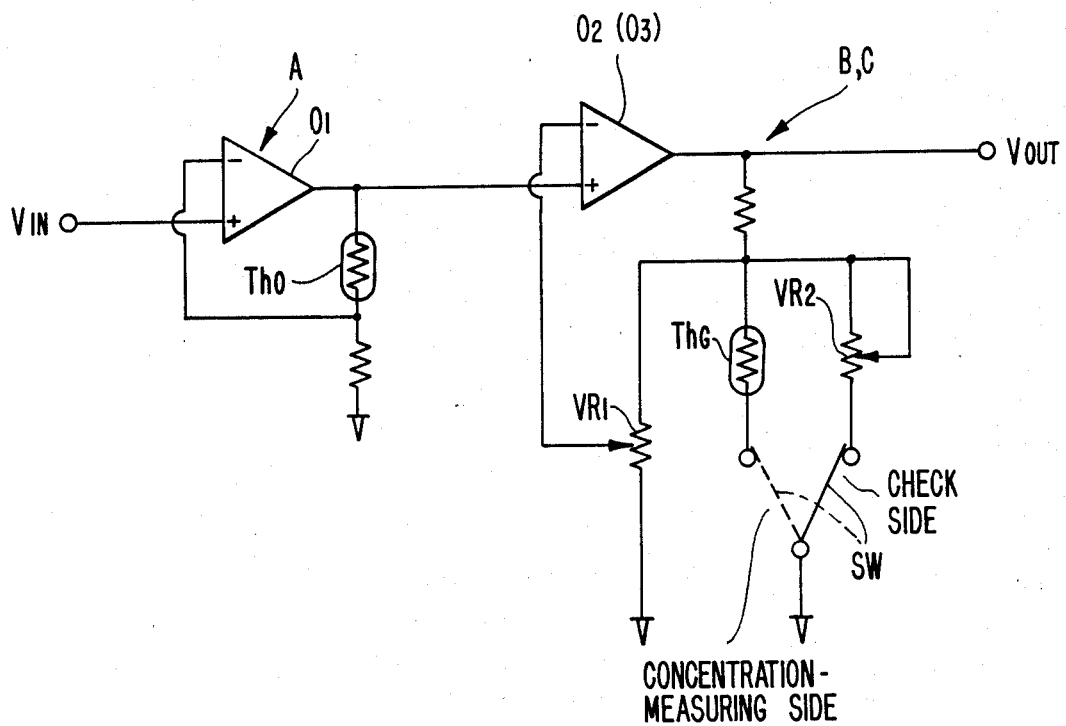
FIG. 2 is a block diagram showing a sensitivity-calibration circuit in an absorption analyzer according to a preferred embodiment of the present invention.
Figure 4:
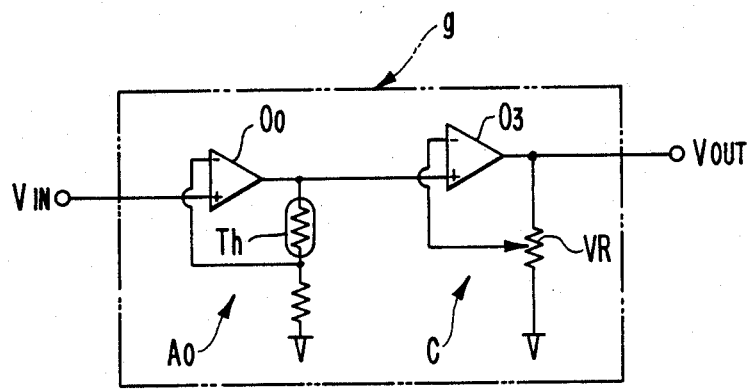
FIG. 4 is a block diagram showing a sensitivity-calibration circuit in an absorption having analyzer the conventional construction.
Figure 3A:
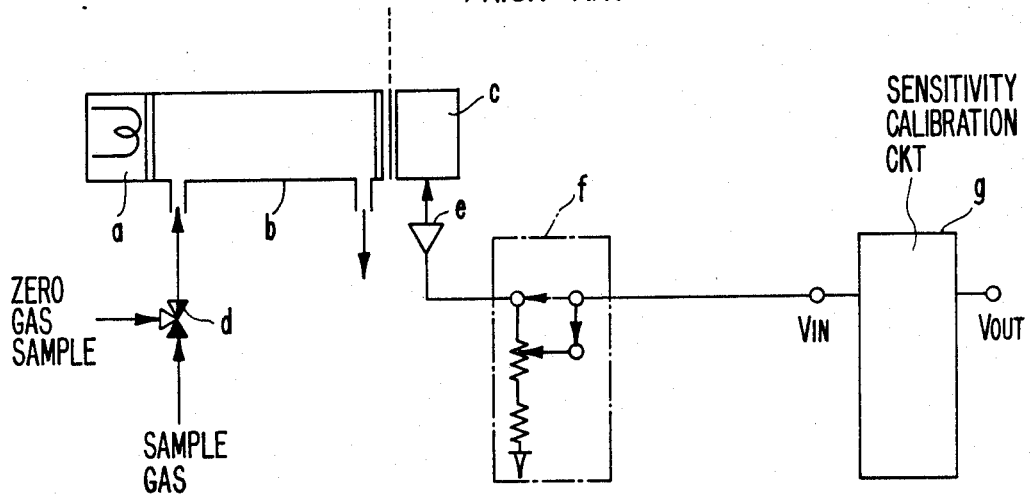
FIGS. 3 (A) and 3 (B) are block diagrams showing a general absorption analyzer.
Figure 3B:
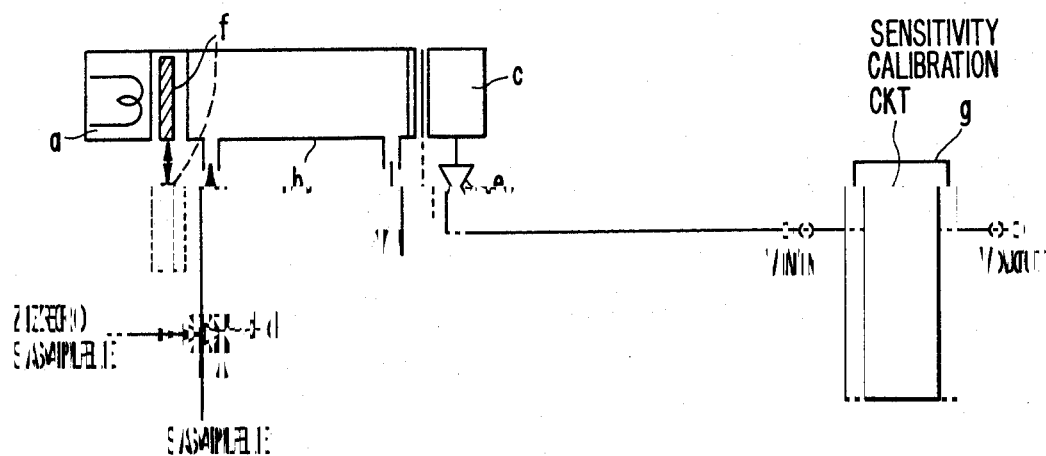

The preferred embodiment of the present invention will be below described with reference to FIG. 2 of drawings.

Figure 1A:
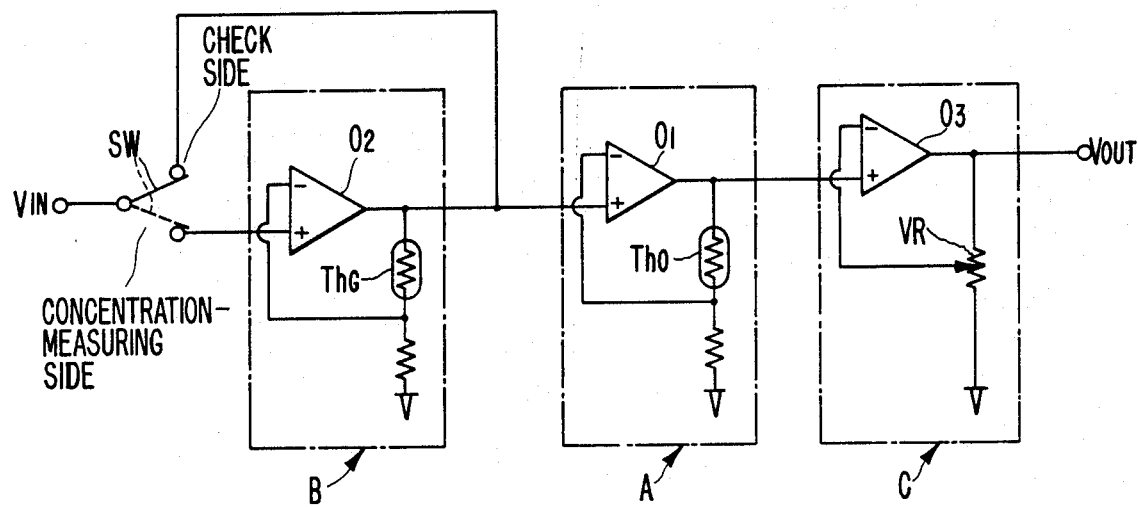
FIGS. 1 (A) and 1 (B) are block diagrams showing a fundamental construction of a sensitivity-calibration circuit in an absorption analyzer according to the present invention.
Figure 1B:
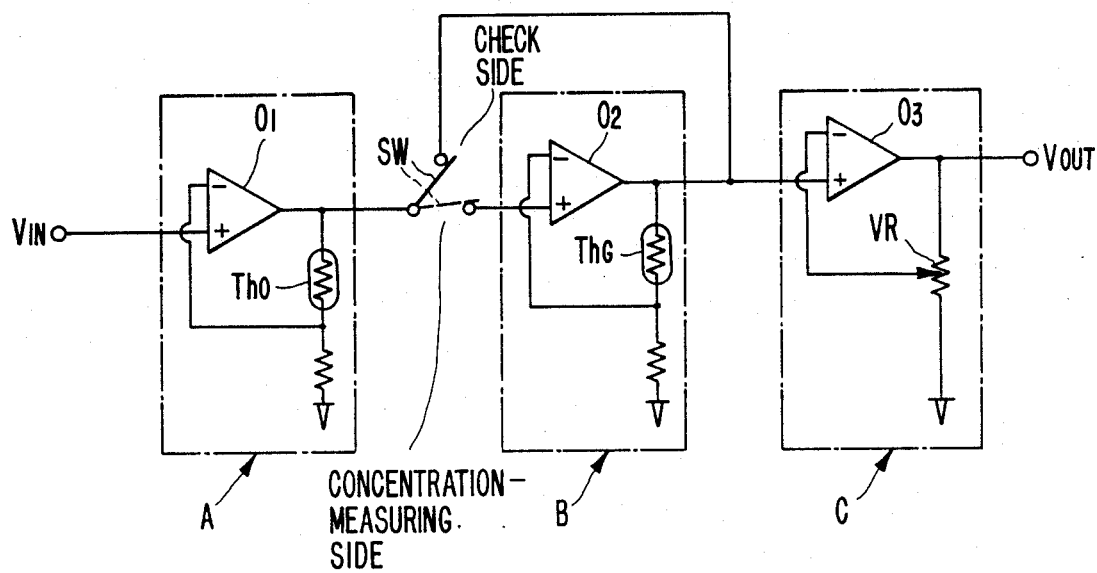

A sensitivity-calibration circuit for use in an absorption analyzer according to the present preferred embodiment comprises a temperature-compensation circuit B for use in a sample system and a sensitivity-adjustment circuit C collectively having a fundamental construction shown in FIG. 1(A) or FIG. 1(B), one operational amplifier being saved by also using an operational amplifier $O_2$ in the temperature-compensation circuit B for use in a sample system as a sensitivity-adjustment amplifier $O_3$ in the sensitivity-adjustment circuit C, and by dividing a sensitivity-adjustment potentiometer VR in the sensitivity-adjustment circuit C into a main sensitivity-adjustment potentiometer $VR_1$ and an auxiliary sensitivity-adjustment potentiometer $VR_2$. Other elements are constructed in a fashion similar to that shown in FIG. 1(A) or FIG. 1(B).

During the regular sensitivity-calibration using the span-calibration sample, the switch SW is arranged so as to be at a concentration-measuring side. In this case, the sample-concentration signal $V_G$, in short $$V_G = c_1 \cdot f(t) \cdot g(t)$$

is given as the input signal $V_{IN}$, wherein $c_1$ is a constant.

Provided that a temperature-drift function of an optical system is f(t) and a temperature-drift function of a sample system is g(t), a gain of a temperature-compensation circuit A for use in a optical system is expressed by K/f(t) while a gain of a temperature-compensation circuit B for use in a sample system and a sensitivity-adjustment circuit C is expressed by $G_1(VR_1)/g(t)$, so that a total gain $G_{TS}$ of the sensitivity-calibration circuit under this condition is expressed by the following equation:

$$G_{TS} = K \ G_1(VR_1)/f(t) \cdot g(t)$$

Accordingly, an output signal $V_{OUT}$ from the sensitivity-calibration circuit during the regular sensitivity-calibration using this span-calibration sample is expressed by the following equation:

$$V_{OUT} = V_G \cdot G_{TS}$$
$$= c_1 \cdot f(t) \cdot g(t) \times K \cdot G_1(VR_1)/f(t) \cdot g(t)$$
$$= c_1 \cdot K \cdot G_1(VR_1)$$

Consequently, any influence due to temperature is eliminated, whereby the output signal $V_{OUT}$ becomes independent of temperature. The main sensitivity-adjustment potentiometer $VR_1$ is operated to adjust $G_1$ $(VR_1)$ so that the output signal $V_{OUT}$ may correspond to a concentration of the span-calibration sample used.

Then, during the first easy check without using the span-calibration sample, the switch SW is arranged so as to be at the check side. In this case, the check signal $V_c$, $$V_c = c_2 \cdot f(t)$$

is given as the input signal $V_{IN}$, wherein $c_2$ is a constant.

At this time, since the thermosensor $TH_G$ in the temperature-compensation circuit B for use in a sample system is not used but the auxiliary sensitivity-adjustment potentiometer $VR_2$ is used, a gain of the temperature-compensation circuit B for use in a sample system and the sensitivity-adjustment circuit C is expressed by $G_1(VR_1) \cdot G_2(VR_2)/f(t)$ and a total gain of the sensitivity-calibration circuit under this condition is expressed by the following equation:

$$G_{TC} = K \cdot G_1(VR_1) \cdot G_2(VR_2)/f(t)$$

Accordingly, the output signal $V_{OUT}$ from the sensitivity-calibration circuit during the easy check without using this span-calibration sample is expressed by the following equation:

$$V_{OUT} = V_G \cdot G_{TC}$$
$$= c_2 \cdot f(t) \times K \cdot G_1(VR_1) \cdot G_2(VR_2)/f(t)$$
$$= c_2 \cdot K \cdot G_1(VR_1) \cdot G_2(VR_2)$$

Consequently, also in this case, temperature influences are eliminated, whereby the output signal $V_{OUT}$ becomes independent of temperature. The auxiliary sensitivity-adjustment potentiometer $VR_2$ is operated to adjust and fix $G_2(VR_2)$ so that this output signal $V_{OUT}$ may take the same value as in the above described regular sensitivity-calibration. In addition, since the ratios of the constants $c_1$ and $c_2$ to a change in sensitivity can be made identical by adjusting the auxiliary sensitivity-adjustment potentiometer $VR_2$, it is necessary in the following easy checks to only operate the main sensitivity-adjustment potentiometer $VR_1$.

However, since the usual measurement is also carried out under the condition that the switch SW is arranged so as to be at the concentration-measuring side, it goes without saying that the output signal $V_{OUT}$ from the sensitivity-calibration circuit becomes independent of temperature in the same manner as in the above described regular sensitivity-calibration.

Furthermore, it goes without saying that the above described sensitivity-calibration circuit according to the present invention can be applied to both the case where the sample is a gas, (e.g.—a gas analyzer) and the case where the sample is a liquid, (e.g.—a liquid analyzer).

What is claimed is:

1. A sensitivity-calibration circuit for an absorption analyzer including an optical system and a sample system and provided with a check-signal generating means for easily checking the sensitivity, said sensitivity-calibration circuit comprising: a temperature-compensation circuit means for said optical system for compensating for a temperature-drift due to said optical system; a temperature-compensation circuit means for said sample system for compensating for a temperature-drift due to said sample system; said temperature-compensation circuit for said optical system and said temperature-compensation circuit for said sample system being separately provided, and a switch means which is switchable to a measuring state, in which both said temperature-compensation circuit for said optical system and said temperature-compensation circuit for said sample system are operative so as to compensate for respective temperature drifts, and is switchable to a checking state in which said temperature-compensation circuit for said sample system is disconnected so as not to be inoperative but said temperature-compensation circuit for said optical system is operative so as to compensate for temperature drift.

2. A sensitivity-calibration circuit for an absorption analyzer as set forth in claim 1, where said temperature-compensation circuit for said sample system comprises an amplifier which is also operative as a sensitivity-adjustment amplifier for adjusting the sensitivity of said sample system.

* * * * *